United States Patent
Tompkins et al.

[11] Patent Number: 6,083,461
[45] Date of Patent: Jul. 4, 2000

[54] REACTION CELL SYSTEM

[75] Inventors: Dale A. Tompkins, Akron; James E. Hall, Mogadore, both of Ohio

[73] Assignee: Bridgestone/Firestone, Inc., Akron, Ohio

[21] Appl. No.: 09/057,113

[22] Filed: Apr. 8, 1998

[51] Int. Cl.[7] .................................................. G01N 21/01
[52] U.S. Cl. .................................. 422/82.05; 422/82.09; 422/103; 436/37
[58] Field of Search .............................. 422/82.05, 82.08, 422/82.09, 102, 103; 436/37, 163, 51

[56] References Cited

U.S. PATENT DOCUMENTS

| | | |
|---|---|---|
| 3,769,178 | 10/1973 | Rothermel, Jr. . |
| 4,798,803 | 1/1989 | Wolcott et al. . |
| 4,950,610 | 8/1990 | Tittle . |
| 5,279,504 | 1/1994 | Williams . |
| 5,470,748 | 11/1995 | Hayden et al. . |
| 5,604,132 | 2/1997 | Capuano et al. . |

*Primary Examiner*—Deborah Jones
*Assistant Examiner*—Jennifer McNeil
*Attorney, Agent, or Firm*—D. A. Thomas

[57] ABSTRACT

A reaction cell system for measurement of catalyst demand includes a spherical chamber having an inlet with a diametrically opposed outlet. An optical cylinder traverses the spherical chamber above an agitator maintained at the bottom thereof. The optical cylinder has a slit passing therethrough adjacent a wall of the spherical cylinder such that laminar and uniform flow of fluid within the chamber passes through the slit. The valving between the inlet and outlet of the chamber is such that the inlet valve opens before and closes after similar actuation of the outlet valve. A source of catalyst and indicator communicate with diaphragm dispensers which are operative to inject precise volumes of catalyst and indicator into the spherical chamber. A valve network allows for passage of the catalyst and indicator into the chamber or into measurement standards. Additionally, the valve network communicates with the source of fluid that feeds the chamber to allow for complete and total flushing of the system.

18 Claims, 1 Drawing Sheet

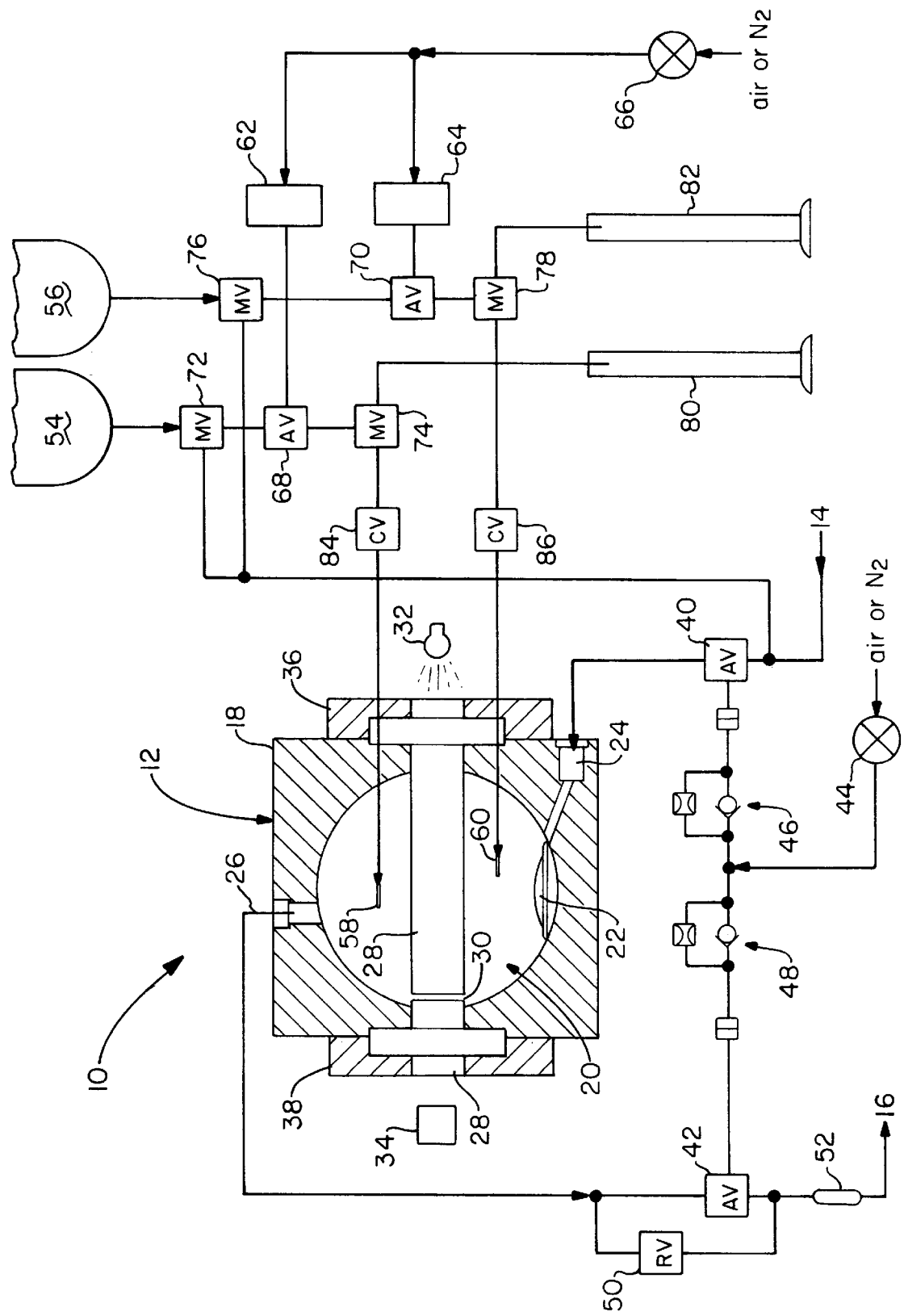

REACTION CELL SYSTEM

TECHNICAL FIELD

The invention herein resides in the art of monitoring and measurement devices. More particularly, the invention relates to the automated measurement of catalyst demand such as that employed for synthesis of synthetic rubber and the like. Specifically, the invention relates to a reaction cell system, in which a catalyst and indicator can be periodically injected into a cell filled with hexane or the like and thereafter be optically monitored to determine, by measuring light absorption, the catalyst demand.

BACKGROUND OF THE INVENTION

A common technique in the production of synthetic rubber and the like is to periodically monitor the effectiveness of the catalyst in the compound through the utilization of a slip stream of hexane or other solvent to a reaction cell, where a catalyst and an indicator are introduced. The reaction cell typically employs a photo-detection technique to measure and monitor the catalyst efficiency, thus indicating the amount of catalyst necessary in the compound to achieve the desired results. Often, a light source and photo-detector are presented on opposite ends of an optical cylinder, across which flow an agitated mixture of the hexane, catalyst and indicator. The output of the photodetector is a function of the efficiency of the catalyst within the system, which equates to catalyst demand.

Prior art reaction cell systems have typically been plagued by several problems. The geometric configuration of such systems has typically been such that it is virtually impossible to make a complete flush of the cell between tests. As a result, reacted material often finds its way into the corners of the reaction cell, adversely impacting the results of subsequent tests. Cleaning of the cells is typically a time consuming and laborious undertaking. Additionally, it is extremely necessary that the amount of catalyst and indicator which is injected into the fixed cavity cell be of a highly accurate measure. Deviations from the desired measure of these ingredients necessarily result in inaccuracies in the test reading, such inaccuracies carrying over to errors in the measure of catalyst demand.

There is a need in the art for a highly accurate reaction cell system which is conducive to ease of cleaning and purging.

DISCLOSURE OF INVENTION

In light of the foregoing, it is a first aspect of the invention to provide a reaction cell system in which the cell cavity is easy to clean and purge.

Another aspect of the invention is the provision of a reaction cell system in which the dispensing valves for injecting catalyst and indicator materials into the cell cavity are of a highly accurate nature.

Another aspect of the invention is the provision of a reaction cell system in which the entire system can be purged by a solvent, such as hexane, and in which the interior of the cell cavity is never exposed to air.

Still a further aspect of the invention is the provision of a reaction cell system in which the timing of hexane flow is such as to assure that the reaction cell cavity is always full.

Yet a further aspect of the invention is the provision of a reaction cell system in which air valves are employed to achieve positive and accurate dispensing, eliminating the possibility of bleedback of the material so dispensed, especially a hazardous environment.

Still an additional aspect of the invention is the provision of a reaction cell system in which manual valves can be employed to select a purging operation, a dispensing measurement operation, or the desired measurement of catalyst demand.

Still another aspect of the invention is the provision of a reaction cell system which is reliable and durable in operation, while being easy to implement with state of the art materials.

The foregoing and other aspects of the invention which will become apparent as the detailed description proceeds are achieved by a reaction cell system for measurement of catalyst demand, comprising: a reaction cell having a spherical chamber therein, said chamber having an inlet and an outlet, said inlet and outlet being substantially diametrically opposed; a source of fluid connected to said inlet through an inlet valve; a return line connected to said outlet through an outlet valve; an optical cylinder traversing said chamber centrally thereof and interposed between said inlet and outlet; an agitator maintained in a lower portion of said spherical chamber, beneath said optical cylinder; a source of catalyst in communication with a catalyst dispenser; a source of indicator in communication with an indicator dispenser; a catalyst injector within said chamber and in operative communication with said catalyst dispenser; an indicator injector within said chamber and in operative communication with said indicator dispenser; and a valve network interposed between said sources of indicator and catalyst, said indicator and catalyst dispensers, and indicator and catalyst injectors to regulate a transfer of precise volumes of indicator and catalyst into said chamber.

Other aspects of the invention which will become apparent herein are attained by a reaction cell system for measurement of catalyst demand, comprising: a reaction cell having a spherical chamber with an inlet and an outlet; a source of fluid connected to said inlet through an inlet valve; a return line connected to said outlet through an outlet valve; an optical cylinder traversing said spherical chamber, said optical cylinder having a gap therein adjacent a wall of said spherical cylinder; an agitator positioned at a bottom portion of said spherical chamber below said optical cylinder; a source of catalyst in communication with a diaphragm catalyst dispenser; a source of indicator in communication with a diaphragm indication dispenser; a three way valve connected to and driving said catalyst and indicator dispensers; a catalyst injector within said spherical chamber and interconnected with said diaphragm catalyst dispenser; an indicator injector within said spherical chamber and interconnected with said diaphragm indicator dispenser; a first valve interposed between said catalyst source, dispenser and injector; and a second valve interposed between said indicator source, dispenser and injector.

BRIEF DESCRIPTION OF THE DRAWING

For a complete understanding of the objects, techniques and structure of the invention reference should be made to the following detailed description and accompanying drawing where an illustrative embodiment of the reaction cell system of the invention is shown.

BEST MODE FOR CARRYING OUT THE INVENTION

Referring now to the drawing, it can be seen that a reaction cell system in accordance with the invention is designated generally by the numeral 10. A primary feature of the system 10 is a reaction cell 12 which is interposed between source and return lines 14, 16 of an appropriate solvent, such as hexane. The reaction cell 12 is employed to perform a titration as will be discussed below.

The reaction cell 12 includes a housing 18 defining a spherical chamber 20 therewith. Maintained near the bottom of the spherical chamber 20 is a magnetic rotor 22, employed to agitate or mix the liquid ingredients introduced into the chamber 20, in standard fashion. An inlet 24 is interconnected with the source line 14 and an outlet 26 is interconnected with the return line 16. The inlet 24 allows for the inflow of hexane into the spherical chamber 20, while the outlet 26 allows for the return thereof to the production system, it being understood that the reaction cell system 20 is interposed within a slip stream in the production system. As will become apparent later, the inlet 24 and outlet 26 provide a means for replenishing the hexane within the spherical chamber 20 and for flushing that chamber, as desired. Moreover, the valving to be discussed later assures that the chamber 20 is always maintained in a "full" posture.

An optical cylinder 28 is maintained within the chamber 20. Preferably, the optical cylinder 28 axially traverses the chamber 20 as shown. As is well known to those skilled in the art, the optical cylinder 28 includes a slit or gap 30 through which material agitated by the rotor 22 will pass. In accordance with the preferred embodiment of the invention, the slit or gap 30 is maintained in juxtaposition to a wall of the spherical chamber 20 to assure that the agitated material passes therethrough. Moreover, the swirling material, agitated by the rotor 22, does not have a vortex, but seeks to flow rather uniformly about the spherical walls, with a return to the rotor through the center of the sphere. Accordingly, the offset of the slit or gap 30 to a position adjacent a wall assures that a consistent flow of material passes therethrough.

A light source 32 and photo-detector 34 are positioned at axially disposed ends of the optical cylinder 28. The light source 32 emits light through the light cylinder 28 and through the material maintained within the slit 30, for reception by the photo-detector 34. The photo-detector 34 is tuned to the characteristic optical wavelength of indicator, such that the photo-detector 34, presents an output corresponding to the light incident thereto. As also shown in the drawing, a pair of end plates or caps 36, 38 are maintained at opposite ends of the housing 18 and serve to secure the optical cylinder 28 in position.

The reaction cell system 10 includes an air actuated valve 40 in the source line 14, and an air actuated valve 42 in the return line 16. As illustrated, a three way valve 44, connected to a source of gas pressure such as air or nitrogen, is interposed between the valves 40, 42 to control the actuation thereof. As further shown, a needle valve flow mechanism 46 is interposed between the three way valve 44 and the air actuated valve 40, with another needle valve flow control mechanism 48 being interposed between the three way valve 44 and the air actuated valve 42. The flow control mechanisms 46, 48 are so configured as to provide a time delay between the actuation and deactuation of the paired valves 40, 42. Particularly, when the three way valve 44 is actuated to apply pressure to the valves 40, 42, the needle-valve flow control mechanism 48 delays the actuation of the valve 42 until after the valve 40 has been actuated. Similarly, when the three way valve 44 is exhausted to remove pressure from the valves 40, 42, the valve 42 is the first to close, followed by the valve 40. It will be appreciated that such time delay achieved by the flow control mechanisms 46, 48 always assures that the spherical chamber 20 is completely filled with hexane. In other words, the return line 16 opens after and closes before the source line 14.

Also positioned within the return line 16 is a relief valve 50 to prevent over pressurization of the spherical chamber 20. Such over pressurization may arise as a result of the time delays incident to the operation of the valves 40, 42, or by the introduction of a catalyst and/or indicator (titrant) which will be discussed below. Also maintained within the return line 16 is a sight glass 52 allowing for visual monitoring of hexane flow.

Also included as a portion of the reaction cell system 10 is a source of catalyst 54 and a source of indicator or titrant 56. As illustrated, the catalyst source 54 is interconnected with an injector 58 for the injecting of precise amounts of catalyst into the spherical chamber 20 of the reaction cell 12. Similarly, the titrant source 56 is interconnected with the injector 60 for similar injections of indicator. It will be appreciated by those skilled in the art that the injectors 58, 60 are syringe-like in structure and use and are employed for the introduction of extremely small metered volumes of the catalyst and indicator.

It will be appreciated that the accuracy of the volumes of catalyst and indicator which are injected into the fixed cavity 20 are extremely important. For this reason, the preferred embodiment of the invention employs diaphragm dispensers 62, 64 which are controlled by an appropriate three way valve 66 for applying gas pressure thereto in the form of air or nitrogen. The dispensing cycles of the diaphragm dispensers 62, 64 are achieved under control of the three way valve 66, while the replenishing of the diaphragm dispensers 62, 64 is achieved on the exhaust of the valve 64 by the fluid pressure of the catalyst and indicator from the sources 54, 56. Those skilled in the art will readily appreciate that the diaphragm dispensers provide for extremely precise dispensing operations, while the implementation of the three way valve 66 assures positive actuation of those dispensers.

Injection of the catalyst and indicator through the associated injectors 58, 60 is achieved by the associated diaphragm dispensers 62, 64 through respectively associated air actuated valves 68, 70. The valves 68, 70 are switched by positive air actuation between passing liquid from the associated source 54, 56 to the respective diaphragms 62, 64 and from those diaphragms to the associated injectors 58, 60. The positive action of the air actuated valves 68, 70 assures that there is no backflow of this liquid and that the full volume maintained within each of the particular diaphragm dispensers 62, 64 is injected into the cavity 20.

As shown, manual valves 72, 74 are maintained in the dispensing line of the catalyst 54, while manual valves 76, 78 are maintained within the dispensing line of the indicator source 56. As shown, manual valves 72, 76 interconnect with the hexane source 14 and, when the valves are actuated to interconnect with the source 14, hexane may be caused to flow throughout the entire system to provide a complete flush of the system, as desired. When the valves 72, 76 are actuated to interconnect respectively with the sources 54, 56, hexane does not enter the flow paths for catalyst and indicator. The manual valves 74, 78 can also be manually actuated to selectively and respectively pass catalyst and indicator to either measurement receptacles 80, 82 or to the associated injectors 58, 60. The measurement receptacles 80, 82 provide standards that can be employed simply to assure that the desired quantities are dispensed by the associated diaphragm dispensers 62, 64.

It may be desired, though not required, to employ check valves 84, 86 in respective injection lines of the catalyst and indicator, as shown. It has been found that the use of the air actuated valves and the three way valves of the system substantially eliminate the need for such check valves.

In normal operation, the manual valves 72, 76 and 74, 78 are switched such that catalyst from the source 54 can be injected through the injector 58 and indicator from the source 56 can be injected from the injector 60. The three way valve 44 is actuated such that the air actuator valve 40 is first opened, followed shortly thereafter by the valve 42. Hexane flows from the source 14 through the inlet 24, flushes the spherical cavity 20, and exits the outlet 26 to the return line 16. After a time sufficient to assure a complete flush has passed, the three way valve 44 is exhausted, with the valve 42 closing and followed shortly thereafter by the valve 40. The relief valve 50 relieves any excessive pressure resulting from the delay in closing between the valves 42, 40. The diaphragm dispensers 62, 64 are actuated by the three way valve 66 to cause precise predetermined volumes of catalyst and indicator to pass through the air actuated valves 68, 70, manual valves 74, 78 and into the cavity 20 via associated injectors 58, 60. Any excessive pressure is relieved by the relief valve 50. The rotor 22 is then actuated to effect a complete blend of the hexane, catalyst and indicator. The blend passes through the slit or gap 30 such that the light impinging upon the photo detector 30 from the source 32 is characteristic of the amount of the catalyst used by impurities in the system - - the remainder being available for use in the chemical process.

It will be appreciated by those skilled in the art that the spherical nature of the cavity 20 precludes any corners or edges for retention of hexane, catalyst and indicator, while assuring a complete flush of the system between tests. The implementation of three way valves assures positive valving and actuation of the injected material as well as the hexane. Additionally, the implementation of diaphragm dispensers assures that precise volumes of catalyst and indicator are injected on each test cycle. The mechanical valving provides a means for completely flushing the entire system, including the diaphragm dispensers and valves with hexane, while assuring that no air reaches the interior of the system to cause adverse reactions.

It will be appreciated that while the embodiment just described has made reference to hexane as the solvent employed, other solvents or fluids may be employed. Indeed, it is contemplated that a styrene monomer in hexane solvent or a butodiene monomer in hexane solvent may be employed. Moreover, the catalyst and indicator may be of any appropriate nature to establish a light absorbing indicator which may be either a single component, or multiple components composition, having an intensity of absorption directly related to the concentration of impurities present in the fluid, such as hexane, being tested.

Thus it can be seen that the objects of the invention have been satisfied by the structure and technique presented above. While in accordance with the patent statutes only the best mode and preferred embodiment of the invention has been presented and described in detail, it is to be understood that the invention is not limited thereto or thereby. Accordingly, for an appreciation of the true scope and breadth of the invention reference should be made to the following claims.

What is claimed is:

1. A reaction cell system for measurement of catalyst demand, comprising:

a reaction cell having a spherical chamber therein, said chamber having an inlet and an outlet, said inlet and outlet being substantially diametrically opposed;

a source of fluid connected to said inlet through an inlet valve;

a return line connected to said outlet through an outlet valve;

an optical cylinder traversing said chamber centrally thereof and interposed between said inlet and outlet;

a source of catalyst in communication with a catalyst dispenser;

a source of indicator in communication with an indicator dispenser;

a catalyst injector within said spherical chamber and in operative communication with said catalyst dispenser;

an indicator injector within said spherical chamber and in operative communication with said indicator dispenser;

an agitator maintained in a lower portion of said spherical chamber, beneath said optical cylinder, said agitator mixing the fluid, the catalyst and the indicator within said spherical chamber to generate a uniform flow of mixed material observable by said optical cylinder, and a valve network interposed between said sources of indicator and catalyst, said indicator and catalyst dispensers, and indicator and catalyst injectors to regulate a transfer of precise volumes of indicator and catalyst into said spherical chamber.

2. The reaction cell system according to claim 1, wherein said optical cylinder has a slit passing therethrough adjacent a wall of said spherical chamber.

3. The reaction cell system according to claim 1, further comprising an actuating valve interposed between said inlet valve and said outlet valve, said actuation valve causing said inlet valve to open before and close after said outlet valve.

4. The reaction cell system according to claim 3, further comprising a first needle valve control mechanism interposed between said actuating valve and said inlet valve, and a second needle valve control mechanism interposed between said actuating valve and said outlet valve, said first and second needle valves effecting time delays in actuation of said inlet and outlet valves.

5. The reaction cell system according to claim 4, wherein said actuating valve is a 3 way valve.

6. The reaction cell system according to claim 5, wherein said fluid is hexane.

7. The reaction cell system according to claim 1, wherein said valve network comprises a first valve interposed between said source of catalyst, catalyst dispenser and catalyst injector, and a second valve interposed between said source of indicator, indicator dispenser and indicator injector, each of said first and second valves sequentially effecting passage from its associated source to its associated dispenser and from said dispenser to its associated injector.

8. The reaction cell system according to claim 7, wherein said catalyst and indicator dispensers comprise diaphragm dispensers.

9. The reaction cell system according to claim 8, further comprising a three way valve connected to and driving said diaphragm dispensers.

10. The reaction cell system according to claim 9, wherein said valve network further comprises first and second diversions valves respectively interposed between said first and second valves and said catalyst and indicator injectors, said diversion valves being operative to divert catalyst and indicator from said injectors to respectively associated measurement standards.

11. The reaction cell system according to claim 10, wherein said valve network further comprises first and second flush valves, each connected to said source of fluid and respectively interposed between said source of catalyst and said first valve and between said source of indicator and said second valve.

12. The reaction cell system according to claim 11, wherein said flush valves are operative to selectively pass said fluid from said source of fluid throughout the reaction cell system under control of said first and second valves, said first and second diversion valves, and said diaphragm dispensers.

13. The reaction cell according to claim 2, further comprising:
   a light source projecting light through one end of said optical cylinder; and
   a photo-detector positioned at an opposite end of said optical cylinder so as to monitor the projected light as it passes through the material passing through said slit.

14. A reaction cell system for measurement of catalyst demand, comprising:
   a reaction cell having a spherical chamber with an inlet and an outlet;
   a source of fluid connected to said inlet through an inlet valve;
   a return line connected to said outlet through an outlet valve;
   an optical cylinder traversing said spherical chamber, said optical cylinder having a gap therein adjacent a wall of said spherical cylinder;
   a source of catalyst in communication with a diaphragm catalyst dispenser;
   a source of indicator in communication with a diaphragm indicator dispenser;
   a three way valve connected to and driving said catalyst and indicator dispensers;
   a catalyst injector within said spherical chamber and interconnected with said diaphragm catalyst dispenser;
   an indicator injector within said spherical chamber and interconnected with said diaphragm indicator dispenser;
   an agitator maintained in a lower portion of said spherical chamber, beneath said optical cylinder, said agitator mixing the fluid, the catalyst and the indicator within said spherical chamber to generate a uniform flow of the mixed material through said gap;
   a first valve interposed between said catalyst source, dispenser and injector; and
   a second valve interposed between said indicator source, dispenser and injector.

15. The reaction cell system according to claim 14, wherein said inlet valve and outlet valve share a common actuator and have associated time delay controls, said inlet valve opening before and closing after said outlet valve.

16. The reaction cell system according to claim 15, further comprising a relief valve in said return line between said outlet and said time delay control.

17. The reaction cell system according to claim 14, wherein said source of fluid is in selective communication with said diaphragm dispensers, said injectors, and said first and second valves.

18. The reaction cell according to claim 14, further comprising:
   a light source projecting light through one end of said optical cylinder; and
   a photo-detector positioned at an opposite end of said optical cylinder so as to monitor the projected light as it passes through the material passing through said gap.

* * * * *